United States Patent [19]
Kim

[11] Patent Number: 5,422,120
[45] Date of Patent: Jun. 6, 1995

[54] HETEROVESICULAR LIPOSOMES

[75] Inventor: Sinil Kim, Solana Beach, Calif.

[73] Assignee: DepoTech Corporation, La Jolla, Calif.

[21] Appl. No.: 78,701

[22] Filed: Jun. 16, 1993

Related U.S. Application Data

[63] Continuation-in-part of Ser. No. 196,590, May 30, 1988, abandoned, which is a continuation-in-part of Ser. No. 496,846, Mar. 21, 1990, abandoned.

[51] Int. Cl.$^6$ .................. A61K 9/127; B01J 13/02
[52] U.S. Cl. ..................... 424/450; 264/4.1; 264/4.3; 264/4.6; 436/829
[58] Field of Search .......... 424/450; 436/829; 264/4.1, 4.3, 4.6

[56] References Cited

U.S. PATENT DOCUMENTS

| | | | |
|---|---|---|---|
| 4,078,052 | 3/1978 | Papahadjopoulos | 424/36 |
| 4,089,801 | 5/1978 | Schneider | 424/450 |
| 4,145,410 | 5/1979 | Sears | 424/19 |
| 4,224,179 | 9/1980 | Schneider | 424/450 |
| 4,235,871 | 11/1980 | Papahadjopoulos | 264/4.1 |
| 4,310,506 | 1/1982 | Baldeschwieler et al. | 424/1 |
| 4,394,372 | 7/1983 | Taylor | 424/450 |
| 4,522,803 | 6/1985 | Lenk et al. | 424/1.1 |
| 4,588,578 | 5/1986 | Fountain et al. | 424/1.1 |
| 4,599,227 | 7/1986 | Dees et al. | 424/38 |
| 4,610,868 | 9/1986 | Fountain et al. | 424/1.1 |
| 4,752,425 | 7/1988 | Martin et al. | 264/4.6 |
| 4,769,250 | 9/1988 | Forssen | 424/450 |
| 4,781,871 | 11/1988 | West, III et al. | 264/4.3 |
| 4,920,016 | 4/1990 | Allen et al. | 424/450 |
| 5,000,959 | 3/1991 | Iga et al. | 424/450 |
| 5,021,200 | 6/1991 | Vanlerberghe et al. | 264/4.3 |
| 5,077,056 | 12/1991 | Bally et al. | 424/450 |
| 5,204,112 | 4/1993 | Hope et al. | 424/450 |
| 5,211,955 | 5/1993 | Legros et al. | 424/450 |

FOREIGN PATENT DOCUMENTS 2050287  1/1991  United Kingdom.

OTHER PUBLICATIONS

Kim, Prep. of Multivesicular Liposomes, BBA, 728, 339 (1983).
CA 107(10) 83830x, 1987, Kim.
Fidler, Drug Carrier Systems, Ed. by Roerdink & Kim, p. 213 (1989).
Huang, Biochemistry, 8:334–352, 1969, "Studies on Phosphatidylcholine Vesicles Formation and Physical Characteristics".
Bang, M., Mol. Bio., 13–238–252, 1965, "Diffusion of univalent ions across the lamellae of swollen phospholipids".
Szoka, et al., Ann. Rev. Biophys. Bioeng., 9:465–508, 1980, "Comparative properties and methods of preparation of lipid vesicles (liposomes)".
Shakiba, et al., Investigative Ophthalmology and Visual Science, 34(10):2903–10, 1993 Sep., "Evaluation of retinal toxicity and liposome encapsulation of the Anti--CMV Drug 2'-nor-cyclic GMP".
Frucht-Perry, et al., Cornea, 11(5):393–7, 1992 Sep., "Fibrin-enmeshed tobramycin liposomes: single application topical therapy of pseudomonas . . . ".
Assil, et al., Investigative Ophthalmology and Visual Science, 32(13):3216–20, 1991 Dec., "Tobramycin liposomes. Single subconjunctival therapy of . . . ".
Assil, et al., Investigative Ophthalmology and Visual Science, 32(11):2891–7, 1991 Oct., "Liposome suppression of proliferative vitreoretinopathy. Rabbit . . . ".
Turski, et al., Magnetic Resonance in Medicine, 7(2):184–96, 1988 Jun., "Magnetic resonance imaging of rabbit brain after intracarotid injection . . . ".

(List continued on next page.)

*Primary Examiner*—Gollamudi S. Kishore
*Attorney, Agent, or Firm*—Spensley Horn Jubas & Lubitz

[57] ABSTRACT

Disclosed are heterovesicular liposomes containing substances of different biologically active compositions each encapsulated in separate chambers of the liposomes, having defined size distribution, adjustable average size, adjustable internal chamber size and number, methods of making them, and treatment of patients with them.

46 Claims, 1 Drawing Sheet

OTHER PUBLICATIONS

Skuta, et al., American Journal of Ophthalmology, 103(5):714–16, 1987, May 15, "Filtering surgery in owl monkeys treated with the antimetabolite . . . ".

Assil, et al., Archives of Ophthalmology, 105(3):400–3, 1987 Mar., "Multivesicular liposomes. Sustained release of the antimetabolite . . . ".

Barbet, et al., Biochimica et Biophysica Acta, 772(3):347–56, 1984, May 30, "Weat acid–induced release of liposome–encapsulated carboxyfluorescein".

Kim., et al., Biochim. Biophys. Acta, 646:1, 1981, "Preparation of cell–size unilamellar liposomes with high captured volume and defined size . . . ".

Kim, et al., Biochim. Biophys. Acta, 728:339–348, 1983, "Preparation of multivesicular liposomes".

Kim., et al., Biochim. Biophys. Acta, 793:801, 1985, "Preparation of multilamellar vesicles of define size––distribution by solvent–spherule . . . ".

Kim., et al., Cancer Treat. Rep., 71:705–711, 1987, "Multivesicular liposomes containing cytarabine entrapped in the presence of . . . ".

Kim., et al., Cancer Research, 47:3935–3937, 1987, "Mutlivesicular Liposomes Containing cytosine arabinoside for slow–release intrathecal therapy".

Kim, et al., Cancer Treat Rep., 71:447–450, 1987, "Multivesicular liposomes containing cytosine arabinoside for slow–release . . . ".

Kim et al., Cancer Chemother Pharmacology, 19:307–310, 1987, "Modulation of the peritoneal clearance of liposomal ara–C by blank liposomes".

Roy, et al., Cancer Cherother. Pharm., 28:105–108, 1991, "Multivesicular liposomes containing bleomycin for subcutaneous administration".

Kim, et al., Reg. Cancer Treat., 2:170–173, 1989, "Intratumoral chemotherapy with multivesicular liposomes containing 1–b–D–arabino . . . ".

Kim, et al., J. Inf. Dis., 162:750–752, 1990, "Multivesicular liposomes for CSF delivery of retroviral agent DDC".

Chamberlain, et al., Archives of Neurol, 50(3):261–264, 1993, "Treatment of leptomeningeal metastasis with intraventricular administration of . . . ".

Chatlut, et al., Cancer Them. Pharmacol., 32:179–182, 1993, "A slow–release methotrexate formation for inrathecal chemotherapy".

Russack, et al., Ann. Neurol., 34:108–112, 1993, "Quantitative cerebrospinal fluid cytology in patients receiving intracavitary chemotherapy".

Kim, et al., J. Clin. Oncol., 11:2186–2193, 1993, "Extended cerebrospinal–fluid cytarabine exposure following intrathecal administration of DTC 101".

Kim, Drugs, 46:618–638, 1993, "Liposomes as carriers of cancer chemotherapy: a review".

Kim, Kim, Kim, Cancer Chemother. Pharmacol., 33:187–190, 1993, "Extended–release formulation of morphine for subcutaneous administration".

Ishii, Liposome Technology, 1:111–121, 1993, "Production and Size Control of Large Unilamellar Liposomes by Emulsification".

Cullis, et al., Phospholipids and Cellular Regulation, 1:65–123, 1985, "Structural properties and functional roles of phospholipids in . . . ".

Bonetti, et al., Cancer Chemotherapy and Pharmacology, In Press, 1993, "An extended–release formulation of methotrexate for subcutaneous . . . ".

Kim, et al., Cancer Res., 53:1596–1598, 1993, "Prolongation of drug action in CSF by encapsulation into multivescicular liposomes".

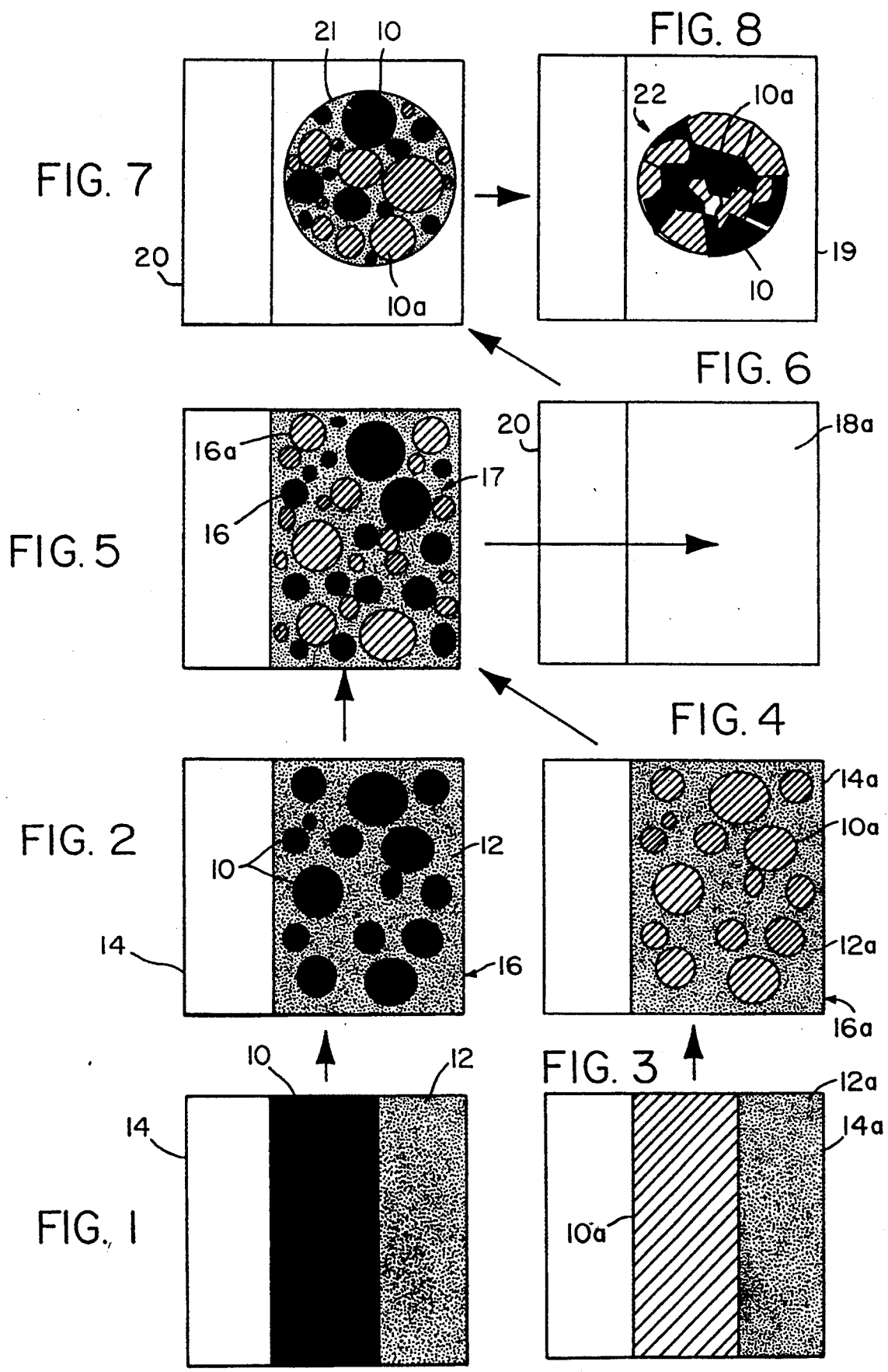

HETEROVESICULAR LIPOSOMES

The present invention is a continuation-in-part of application Ser. No. 196,590, filed May 30, 1988, which in turn is a continuation-in-part application of application Ser. No. 496,846, filed Mar. 21, 1990, all abandoned in favor of this application.

FIELD OF THE INVENTION

The invention relates to the synthetic heterovesicular lipid vesicles or liposomes, processes for their manufacture and encapsulation of various materials therein, and treatment of patients with them.

BACKGROUND ART

Multivesicular liposomes are one of the three main types of liposomes, first made by Kim, et al. (*Biochim, Biophys. Acta*, 782:339–348, 1983), and are uniquely different from the unilamellar (Huang, *Biochemistry*, 8:344–352, 1969; Kim, et al. *Biochim. Biophys. Acta*, 646:1–10, 1981) and multilamellar (Bangham, et al., *J. Mol, Bio.*, 13:238–252, 1965) liposomes in that there are multiple non-concentric aqueous chambers within. Previously described techniques for producing liposomes relate to the production of non-multivesicular liposomes; for example, U.S. Pat. Nos. 4,522,803—Lenk, 4,310,506—Baldeschwieler, 4,235,871—Papahadjopoulos, 4,224,179—4,078,052—Papahadjopoulos, 4,394,372—Taylor, 4,308,166—Marchetti, 4,485,054—Mezei, and 4,508,703—Redziniak. For a comprehensive review of various methods of liposome preparation, refer to Szoka, et al. (*Ann. Rev. Biophys. Bioeng.*, 9:467–508, 1980).

Heterovesicular liposomes are lipid vesicles or liposomes with multiple internal aqueous chambers where at least two substances of different compositions are each encapsulated in separate chambers within one liposomes. The lipid vesicles or liposomes with multiple internal aqueous chambers include, but are not limited to, multilamellar liposomes, stable paucilamellar liposomes, and multivesicular liposomes. It is highly advantageous to provide a liposome delivery system in which two or more different substances are each encapsulated in separate compartments of a single liposome rather than encapsulated together in each compartment of the liposome.

SUMMARY OF THE INVENTION

The composition of the present invention comprises heterovesicular liposomes, i.e. lipid vesicles or liposomes with multiple internal aqueous chambers where two or more substances of different compositions are each encapsulated separately in different chambers within one liposome.

Briefly, the method of the invention comprises making a "water-in-lipid" emulsion by dissolving amphipathic lipids in one or more organic solvents for the first lipid component, adding an immiscible first aqueous component including a substance to be encapsulated, preferably in the presence of a halogenohydroacid and then emulsifying the mixture mechanically. As used herein, the term "halogenohydroacid" means an acid represented by the formula HX, wherein X is a halogen (e.g., Br, F, Cl, I). The halogenohydroacids are typically obtained by dissolving the corresponding hydrogen halides (which can also be expressed as HX) in water. The preferred halogenohydroacid is hydrochloric acid (HCl).

In the emulsion, the water droplets suspended in the organic solvent will form the internal aqueous chambers, and the monolayer of amphipathic lipids lining the aqueous chambers will become one leaflet of the bilayer membrane in the final product. A second lipid component is then formed by dissolving amphipathic lipids in a volatile organic solvent and adding an immiscible second aqueous component including a second substance to be encapsulated, preferably in the presence of halogenohydroacid. A second emulsion is then created. A chimeric emulsion is then formed by combining the first and second emulsions. The chimeric emulsion consists of multiple water droplets suspended in organic solvent where the substances of two different compositions are each dissolved separately in different aqueous droplets. The chimeric emulsion is then immersed in a third aqueous immiscible component preferably containing one or more nonionic osmotic agents and acid-neutralizing agent of low ionic strength and then mechanically dividing it to form solvent spherules suspended in the third aqueous component. The solvent spherules contain multiple aqueous droplets where the substances of two different compositions are each dissolved separately in different aqueous droplets within a single solvent spherule. The volatile organic solvent is evaporated from the spherules preferably by passing a stream of gas over the suspension. When the solvent is completely evaporated, the spherules convert into heterovesicular liposomes with multiple internal aqueous chambers where two substances of different compositions are encapsulated separately in different chambers within one liposome.

The use of halogenohydroacid with a neutralizing agent, or other forms of halides or other small anions which slow leakage rates, is preferably for high encapsulation efficiency and for a slow leakage rate of encapsulated molecules in biological fluids and in vivo. It is also preferable to use neutralizing agent of low ionic strength to prevent solvent spherules from sticking to each other.

Accordingly, it is an object of the present invention to provide a heterovesicular lipid vesicle or liposome having at least two substances of different compositions each encapsulated separately in different chambers of the vesicle or liposome.

A further object of the present invention is the provision of a heterovesicular liposome containing at least two biologically active substances of different compositions each encapsulated separately in chambers of the liposome in the presence of halogenohydroacid or other forms of halides or other small anions which slow the leakage of them.

It is a further object of the present invention to provide a heterovesicular liposome containing at least two biologically active substances of different compositions each encapsulated separately in chambers of the liposome in the presence of halogenohydroacid or other forms of halides or other small anions and a neutralizing agent.

It is a further object of the present invention to provide methods of producing such heterovesicular lipid vesicles or liposomes.

It is a further object of the present invention to provide processes for producing such heterovesicular lipid vesicles or liposomes by providing a first lipid component dissolved in one or more organic solvents and adding to the lipid component an immiscible first aqueous component containing a first substance to be encapsulated, forming a first water in oil emulsion from the first two immiscible components, providing a second lipid component dissolved in one or more organic solvents and adding into the lipid component an immiscible second aqueous component containing a second substance to be encapsulated, forming a second water in oil emulsion from the second two immiscible components, forming a chimeric emulsion by combining the first water in oil emulsion and second water in oil emulsion, transferring and immersing the chimeric emulsion into a third immiscible aqueous component, dispersing the chimeric emulsion to form solvent spherules containing multiple droplets of the first aqueous component containing the first substance and the second aqueous component containing the second substance, and evaporating the organic solvent from the solvent spherules to form the heterovesicular lipid vesicles or liposomes.

It is a further object to provide such a process in which a variety of hydrophilic biologically active materials and can be encapsulated separately in chambers of the heterovesicular lipid vesicles or liposomes.

It is a further object of the present invention to provide a method for the treatment of a patient with at least two separate biologically active substances of different compositions by administering them to the patient encapsulated separately in chambers of a heterovesicular vesicle or liposome.

Other and further objects, features and advantages of the invention appear throughout the specification and claims.

BRIEF DESCRIPTION OF THE DRAWINGS

The drawing is a schematic diagram illustrating preparation of a heterovesicular vesicle or liposome.

FIG. 1 is a schematic representation of a first aqueous substance added to a first lipid component in a vial.

FIG. 2 is a schematic representation of a first water in oil emulsion containing the aqueous substance and lipid components of FIG. 1.

FIG. 3 is a schematic representation of a two phase system in a vial containing a second aqueous component and a second lipid component.

FIG. 4 is a schematic representation of a water in oil emulsion formed from the aqueous component and lipid component of FIG. 3 by shaking.

FIG. 5 is a schematic representation of a chimeric emulsion made by mixing together the water in oil emulsion of FIG. 2 and the water in oil emulsion of FIG. 4.

FIG. 6 is a schematic representation of a vial containing an immiscible aqueous component into which the chimeric emulsion of FIG. 5 is introduced.

FIG. 7 is a schematic representation of solvent spherules containing droplets of the first and second aqueous components.

FIG. 8 is a schematic representation of the heterovesicular liposome formed by evaporation of solvent from the solvent spherules of FIG. 7.

DESCRIPTION OF PREFERRED EMBODIMENT

The term "multivesicular liposomes" as used throughout the specification and claims means man-made, microscopic lipid-vesicles consisting of lipid bilayer membranes, enclosing multiple non-concentric aqueous chambers which all contain the same component. In contrast, the term "heterovesicular liposomes" as used throughout the specification and claims means man-made, microscopic liquid vesicles consisting of lipid bilayer membranes enclosing multiple, aqueous chamber wherein at least two of the chambers separately contain substances of different compositions. The microscopic lipid vesicles include but are not limited to multilamellar liposomes, stable paucilamellar liposomes, and multivesicular liposomes.

The term "chimeric emulsion" as used throughout the specification and claims means an emulsion that consists of multiple water droplets suspended in organic solvent where the substances of two different compositions are each dissolved separately in different aqueous droplets.

The term "solvent spherule" as used throughout the specification and claims means a microscopic spheroid droplet of organic solvent, within which is multiple smaller droplets of aqueous solution. The solvent spherules are suspended and totally immersed in a second aqueous solution.

The term "neutral lipid" means oil or fats that have no membrane-forming capability by themselves and lack a hydrophilic "head" group.

The term amphipathic lipids means those molecules that have a hydrophilic "head" group and hydrophobic "tail" group and have membrane-forming capability.

The composition of the present invention is a heterovesicular lipid vesicle or liposome having at least two substances of different compositions each encapsulated separately in different chambers of the vesicle or liposome.

Many and varied biological substances can be incorporated by encapsulation within the multivesicular liposomes. These include drugs, and other kinds of materials, such as DNA, RNA, proteins of various types, protein hormones produced by recombinant DNA technology effective in humans, hematopoietic growth factors, monokines, lymphokines, tumor necrosis factor, inhibin, tumor growth factor alpha and beta, mullerian inhibitory substance, nerve growth factor, fibroblast growth factor, platelet-derived growth factor, pituitary and hypophyseal hormones including LH and other releasing hormones, calcitonin, proteins that serve as immunogens for vaccination, and DNA and RNA sequences.

The following Table 1 includes a list of representative biologically active substances which can be encapsulated in heterovesicular liposomes in the presence of a hydrohalide and which are effective in humans.

TABLE 1

| Antiasthmatics | Antiarrhythmics | Tranquilizers |
|---|---|---|
| melairoterenol | propanolol | chlorpromazine |
| aminophylline | atenolol | benzodiazepine |
| theophylline | verapamil | butyrophenones |
| terbutaline | Antianginas | hydroxyzines |
| norepinephrine | isosorbide dinitrate | meprobamate |
| ephedrine | Hormones | phenothiazines |

TABLE 1-continued

| | | |
|---|---|---|
| isoproterenol | thyroxine | thioxanthenes |
| adrenalin | corticosteroids | Steroids |
| Cardiac glycosides | testosterone | preunisone |
| digitalis | estrogen | triamcinolone |
| digitoxin | progesterone | hydrocortisone |
| lanatoside C | mineralocorticoid | dexamethasone |
| digoxin | Antidiabetics | betamethasone |
| Antihypertensives | Diabenese | preunisolone |
| apresoline | insulin | Antihistamines |
| atenolol | Antineoplastics | pyribenzamine |
| captopril | azathioprine | chlorpheniramine |
| reserpine | bleomycin | diphenhydramine |
| Antiparasitics | cyclophosphamide | Sedatives and Analgesics |
| praziquantel | vincristine | morphine |
| metronidazole | methotrexate | dilaudid |
| pentamidine | 6-TG | codeine |
| ivermectin | 6-MP | codeine-like synthetics |
| Nucleic Acids and Analogs | vinblastine | demerol |
| DNA | VP-16 | oxymorphone |
| RNA | VM-26 | phenobarbital |
| methylphosphonates and | cisplatin | barbiturates |
| analogs | 5-FU | fentanyl |
| Antisense nucleic acids | FUDR | ketorolac |
| Antibiotics | fludarabine phosphate | Vasopressors |
| penicillin | Immunomedalators | dopamine |
| tetracycline | interferon | dextroamphetamine |
| amikacin | interleukin-2 | Antivitals |
| erythromycin | gammaglobulin | acyclovir and derivatives |
| cephalothin | monoclonal antibodies | Gancyclovir and phosphates |
| imipenem | Antifungals | Winthrop-51711 |
| cefotaxime | amphotericin B | ribavirlin |
| carbenicillin | myconazole | rimantadine/amantadine |
| ceftazidime | muramyl dipeptide | azidothymidine & derivates |
| kanamycin | clotrimazole | adenine arabinoside |
| tobramycin | ketoconazole | amidine-type protease |
| ampicillin | fluconazole | inhibitors |
| gentamycin | itraconazole | |
| cefoxitin | | |
| cefadroxil | | |
| cefazolin | | |
| other aminoglycosides | | |
| amoxicillin | | |
| moxalactam | | |
| piperacillin | | |
| vancomycin | | |
| ciprofloxacin | | |
| other quinolones | | |

Vaccines other recombinant, killed and live vaccines and antigenic material for use
as vaccines.
antigenic material for the treatment of allergies
influenza
respiratory syncytial virus
HIV vaccine
Hemophilus influenza vaccines
Hepatitis A,B,C vaccines
mumps
rubella
measles
tetanus
malaria vaccines
herpes
cancer vaccines
Anti-leu-3a vaccine Monoclonal Antibodies (human, mouse other species-derived and/or recombinant and/or fusions and/or fragments thereof)

OKT3
OKT4
HA-IA
Anti-Carcino-Embryonic Antigen Antibodies
Anti-Ganglioside Antibodies: Anti GD2, Anti GM2, Anti GD3, Anti GM3
Urinary Tract-Associated Antigen-related antibodies
Anti-Il-2 Receptor
Chimeric Anti-Leu-2
Anti-IL-2 receptor
Anti-Leu-2
Chimeric Anti-Leu-3a
Chimeric L6
MAb-L6

TABLE 1-continued

Radiolabeled L6
Centorex
Centoxin
Panorex
Anti-LPS
Immunotoxin
Anti-tumor necrosis factor
Anti-pseudomonas
Anti-tumor necrosis factor
OncoRad 103
OncoScint CR103
OncoScint OV103
OncoScint PR356
OncoTher 130
KS 1/4-DAVLB
ADCC agent
Murine monoclonal antibodies to human B-cell lymphomas (anti-idiotypes)
Murine monoclonal antibody (1Melpg1) (anti-idiotype) against murine monoclonal
antibody to melanoma-associated antigen
Anti-B4-blocked ricin
Anti-My9-blocked ricin
ImmuRaid-CEA
MAb against colorectal, ovarian, and lung cancers
rhenium-186 MAb
Orthoclone OKT ®
E5 ™
LYM-1
TNT
XomaZyme ®-791
XomaZyme ®-CD5 Plus
XomaZyme ®-CD7 Plus
XomaZyme ®-Mel Herbicides Triazine
chloroacetamide
cyanazine
bentazone
Roundup
Rodeo
butachlor
CNP
chlomethoxynil
simetryne
Atrazine
Alachlor
Cyanazine
metolachlor
metribuzin
phenoxy herbicides: 2,4-D [(2,4-dichlorophenoxy)acetic acid],
2,4-D amine (2,4-dichlorophenoxyacetic acid dimethylamine),
2,4-D isooctyl (2,4-dichlorophenoxyacetic acid isooctyl ester),
2,4,5-T amine (2,4,5-trichlorophenoxyacetic acid trimethylamine)
other triazine herbicides
other chloroacetamide herbicides
other phenoxyacid herbicides Pesticides Abamectin
other avermectins
atrazine
lindane
dichlorvos
dimethoate
warfarin
p,p'-DDD
p,p'-DDE
HCH
DMDT
aldrin
dieldrin
Aldicarb
EDB
DCP
DBCP
simazine
cyanazine
*Bacillus thuringiensis* toxin
*Bacillus thuringiensis* var. *kurstaki*
bis(tri-n-butyltin)oxide (TBTO)
other organochlorine pesticides Proteins and Glycoproteins lymphokines
interleukins - 1, 2, 3, 4, 5, 6, 7, 8, 9, 10, 11.

TABLE 1-continued cytokines
GM-CSF
M-CSF
G-CSF
tumor necrosis factor
inhibin
tumor growth factor
Mullerian inhibitors substance
nerve growth factor
fibroblast growth factor
platelet derived growth factor
coagulation factors (e.g. VIII, IX, VII)
insulin
tissue plasminogen activator
histocompatibility antigen
oncogene products
myelin basic protein
collagen
fibronectin
laminin
other proteins made by recombinant DNA technology
erythropoietin
IL-3/GM-CSF fusion proteins
Monoclonal antibodies
Polyclonal antibodies
antibody-toxin fusion proteins
antibody radionuclide conjugate
Interferons
Fragments and peptide analogs, and analogs of fragment of proteins, peptides
and glycoproteins.
Epidermal growth factor
CD4 receptor and other recombinant receptors
other proteins isolated from nature
Antidiuretic hormone
oxytocin
adrenocorticotropin Hormone
calcitonin
follicle stimulating hormone
luteinizing hormone releasing hormone
luteinizing hormone
gonadotrophin
transforming growth factors
streptokinase
Human Growth Hormone,
Somatotropins for other species, including, but not limited to:
    1. Porcine,
    2. Bovine,
    3. Chicken,
    4. Sheep,
    5. Fish,
Growth Hormone releasing hormones for humans and various animal species,
Glucagon,
Desmopressin,
Thyroid Releasing Hormone,
Thyroid Hormone,
Secretin,
Magainins,
Integrins,
Adhesion Peptides, including, but not limited to, those having the
Arginine-Glutamine-Aspartic Acid sequence,
Super Oxide Dismutase,
Defensins,
T-Cell Receptors,
Bradykinin antagonists,
Pentigetide,
Peptide T,
Antinflammins,
Major Histocompatibility (MHC) complex components and peptides
targeted to the MHC,
Protease inhibitors,
Lypressin,
Buserelin,
Leuprolide,
Nafarelin,
Deslorelin,
Goserelin,
Historelin,
Triptorelin,
LHRH antagonists,
HOE-2013,
Detirelix,
Org-30850,

TABLE 1-continued

ORF-21243,
Angiotensin Converting Enzyme inhibitor Peptide,
Renin inhibitory peptides,
Ebiratide (HOE-427),
DGAVP,
Opiate receptor agonists and antagonists, including, but not limited to:
    1. Enkephalins,
    2. Endorphins,
E-2078,
DPDPE,
Vasoactive intestinal peptide,
Atrial Natriuretic Peptide,
Brain Natriuretic Peptide,
Atrial Peptide clearance inhibitors,
Hirudin,
Oncogene Inhibitors,
Other Colony Stimulating Factors,

| Neurotransmitters | Radionuclides | Radio contrasts |
|---|---|---|
| Dopamine | Technetium | Gadolinium chelates |
| Epinephrine | Indium | Iohexol |
| Norepinephrine | Yttrium | Ethiodol |
| acetylcholine | Gallium | Iodexinol |
| Gammaamino butyric acid | | |

Others
amino acids
vitamins
cell surface receptor blockers

As used herein, the term "biologically active", when used to describe substances present in the chambers of the heterovesicular liposome, includes substances which possess biological activity in the form as presented in the vesicle as well as substances which become active after release from the vesicle chamber (i.e., possess "quiescent" biological activity). For example, in the latter instance, a first vesicle chamber could contain an enzyme and a second vesicle chamber could contain a prodrug which is converted upon interaction with the enzyme into an active moiety with therapeutic activity. Alternatively, the invention embraces a first vesicle chamber containing a substance possessing quiescent biological activity and a second vesicle chamber containing a substance possessing a different quiescent biological activity; where, upon release from their respective chambers, the substances interact with each other or components of the in vivo biological melieu such that both substances become biologically active in vivo. For example, a first vesicle chamber could contain the inactive compound 5-fluorocytosine (5-FC) and a second vesicle chamber could contain the enzyme cytosine deaminase. When cytosine deaminase is release from its vesicle and interacts with 5-FC released from its vesicle, the biologically active antitumor drug 5-fluorouracil (5-FU) is produced.

In addition, biologically active substances which can be incorporated include substances which act indirectly. For example, various excipients and stabilizers may be present. Such substances may act, for example, to increase the shelf life or bioavailability of a particular drug. Alternatively, many substances commonly classified as excipients may actually possess direct biological activity from very slight to quite significant. For example, the common excipient mannitol can also act biologically as a diuretic and even water may act biologically to affect dehydration. Such indirectly active substances include aqueous or non-aqueous solutions, suspensions, and emulsions. Examples of non-aqueous solutions are propylene glycol, polyethylene glycol, vegetable oils such as olive oil, and injectable organic esters such as ethyl oleate. Aqueous carriers include water, alcoholic-aqueous solutions, emulsions or suspensions, including saline and buffered media. Parenteral vehicles include sodium chloride solution, Ringer's dextrose, dextrose, and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like (see, Remingtons Pharmaceutical Sciences, 16th Ed., A. Oslo, ed., Mack, Easton, PA. 1980). Those of ordinary skill in the art can readily ascertain and envision various combinations of compounds which can be utilized in the vesicles of the invention without resorting to undue experimentation.

A preferred method of making the heterovesicular vesicle or liposome is illustrated in the drawing to which reference is now made. As shown in FIG. 1, in step 1 a first aqueous substance of composition 10 to be encapsulated is added to a first lipid component 12 in the vial 14. The vial 14 is sealed and in step 2 is mixed and shaken, such as being attached to the head of a vortex mixer to form the first water in oil emulsion 16 shown in FIG. 2 containing the first substance of composition 10 to be encapsulated. In a second vial 14a, a second aqueous 10a to be encapsulated is added to a second lipid component 12a, as shown in FIG. 3, and the vial 14a is sealed and in step 4 is mixed, such as being attached to the head of a vortex mixer to form a second water-in-oil emulsion 16a containing the substance of composition 10a to be encapsulated.

In step 5 the first 16 and second 16a water in oil emulsions are added together and mixed, such as by hand to make a "chimeric" emulsion as shown in FIG. 5.

In step 6, as shown in FIG. 6 a portion of the chimeric emulsion from step 5 is individually added to vials 20 containing a third immiscible aqueous component 18a such as by squirting rapidly through a narrow tip pasteur pipette into two one-dram vials, here shown as one.

In step 7 vials from step 6 are shaken, such as by a vortex mixer, and in step 8 the chloroform spherule suspension 21 (as shown in FIG. 7), in each vial is transferred from step 7 and the chloroform is evaporated, such as by a stream of nitrogen gas, thereby providing the heterovesicular liposome 22 (as shown in FIG. 8), that contains a first substance in one or more internal aqueous chambers and a second substance in the remaining internal aqueous chambers within a single liposome.

Preferably, each of the substances to be encapsulated are encapsulated in the presence of a halogenohydroacid, such as hydrochloric acid, which slows their leakage rate from the liposome or vesicle. Most preferably, the halogenohydroacid is HCl, HI, or HBr. Other hydrochlorides which are satisfactory include, but not limited to, guanine hydrochloride, glucosamine hydrochloride, lysine hydrochloride, histidine hydrochloride, arginine hydrochloride, and combinations thereof, which can be neutral, acidic, or basic.

As previously mentioned, any biologically active substance, such as illustrated in Table 1, can be encapsulated separately in chambers of the vesicle or liposome.

The heterovesicular liposomes may be administered by any desired route; for example, intrathecal, intraperitoneal, subcutaneous, intravenous, intralymphatic, oral, and submucosal, under many different kinds of epithelia including the bronchialar epithelia, the gastrointestinal epithelia, the urogenital epithelia, and various mucous membranes of the body, and intramuscular.

The heterovesicular liposomes may be modified in order to impart organ or cell target specificity. Such modifications may be particularly relevant for using the vesicles of the invention to administer drugs which are highly toxic or capable of inducing severe side effects, such as taxol or other anti-neoplastic agents which might otherwise not be utilized in view of their deleterious effects on normal tissues when systemically disseminated.

The targeting of liposome has been classified based on anatomical and mechanistic factors. Anatomical classification is based on the level of selectivity, for example, organ-specific, cell-specific, and organelle-specific. Mechanistic targeting can be distinguished based upon whether the targeting is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization (see, for example, Remington's Pharmaceutical Sciences, Gannaro, A. R., ed., Mack Publishing, 18 Edition, pp. 1691-1693, 1990, incorporated by reference).

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand (Mannino, et al., *Bio Techniques*, 6(7):682, 1988, incorporated by reference). The compounds bound to the surface of the targeted delivery system may vary from small haptens of from about 125-200 molecular weight to much larger antigens with molecular weights of at least about 6 KD, but generally of less than $10^6$ KD. Proteinaceous ligand and receptors are of particular interest.

In general, surface membrane proteins which bind to specific effector molecules are referred to as receptors. In the present invention, antibodies are preferred receptors (U.S. Pat. Nos. 4,806,466 and 4,957,735; incorporated by reference). Antibodies can be used to target liposomes to specific cell-surface ligands. For example, certain antigens expressed specifically on tumor cells, referred to as tumor-associated antigens (TAAs), may be exploited for the purpose of targeting antibody-containing liposomes directly to malignant tumor. Since the composition incorporated in the liposome may be indiscriminate with respect to cell type in its action, a targeted delivery system offers a significant improvement over randomly injecting non-specific liposomes. A number of procedures can be used to covalently attach either polyclonal or monoclonal antibodies to a liposome bilayer. Antibody-targeted liposomes can include monoclonal or polyclonal antibodies or fragments thereof such as Fab, or F(ab')$_2$, as long as they bind efficiently to the antigenic epitope on the target cells. Liposomes may also be targeted to cells expressing receptors for hormones or other serum factors (Malone, et al., *Proc. Nat'l. Acad. Sci, USA,*,86:6077, 1989; Gregoriadis, *Immunology Today*, 11(3):89, 1990; both incorporated by reference).

The following examples set forth presently preferred methods of encapsulating two substances of different compositions in separate chambers of a vesicle or liposome.

EXAMPLE 1

Preparation of Dideoxycytidine Glucose Heterovesicular Liposomes

Step 1: A first aqueous substance (one ml of 20 mg/ml dideoxycytidine solution in water with 0.1N hydrochloric acid) was added into a one-dram vial containing the first lipid component (9.3 umoles of dioleoyl lecithin, 2.1 umoles of dipalmitoyl phosphatidylglycerol, 15 umoles of cholesterol, 1.8 umoles of triolein and one ml of chloroform).

Step 2: The first vial was sealed and attached to the head of a vortex mixer and shaken at maximum speed for 6 minutes to form the first water-in-oil emulsion.

Step 3: In second vial, the second aqueous substance (one ml of 30 mg/ml glucose solution in water with 0.1N hydrochloric acid) was added into the second lipid component (which is identical to the first lipid component).

Step 4: The second vial was sealed and attached to the head of a vortex mixer and shaken at maximum speed for 6 minutes to form the second water-in-oil emulsion.

Step 5: 0.5 ml of the first emulsion was added to the second vial and mixed by hand to make a "chimeric" emulsion.

Step 6: Half of the "chimeric" emulsion was individually squirted rapidly through a narrow tip Pasteur pipette into one-dram vials, each containing a third immiscible aqueous component (2.5 ml water, 32 mg/ml glucose, 40 mM free-base lysine.

Step 7: The vials from step 6 were shaken on the vortex mixer for 3 seconds at "5" setting to form solvent spherules containing multiple droplets of the first and second aqueous substances within.

Step 8: The chloroform spherule suspensions in each vials were transferred into the bottom of a 2 L beaker containing 4.5 ml of water, 35 mg/ml glucose, and 22 mM free-base lysine. A stream of nitrogen gas at 7 L/min was flushed through the beaker to evaporate chloroform over 5 minutes at 15 deg. C.

The above example describes a method of making heterovesicular liposomes which separately contain glucose in approximately 5/6 of the internal aqueous chambers and separately contain dideoxycytidine in the remaining 1/6 of the internal aqueous chambers within a single liposome. Heterovesicular liposomes containing dideoxycytidine solution as one aqueous substance and glucose as the second aqueous substance were markedly more stable than non-heterovesicular liposomes.

EXAMPLE 2

This example is for the synthesis of heterovesicular liposomes containing IL-2 (interleukin-2) and lysine hydrochloride: For each batch of liposomes prepared, one ml of water containing 10 mg/ml HSA (Human serum albumin), 1 ug of IL-2,200 mM lysine HCl pH 7.13 was added into a one-dram vial containing 9.3 umoles of dioleoyl lecithin, 2.1 umoles of dipalmitoyl phosphatidylglycerol, 15 umoles of cholesterol, and 1.8 umoles of triolein and one ml of chloroform (this is the first water-in-oil emulsion). For the second water-in-oil emulsion, 1 ml of lysine HCl (without IL-2) was added into one-dram vial containing 9.3 umoles of dioleoyl lecithin, 2.1 umoles of dipalmitoyl phosphatidylglycerol, 15 umoles of cholesterol, and 1.87 umoles of triolein and one ml of chloroform. Each of the two vials were individually attached to the head of a vortex mixer and shaken sequentially at the maximum speed for 6 minutes.

0.5 ml of the first water-in-oil emulsion was added to the 2 ml of the second emulsion and mixed to make a "chimeric" water-in-oil emulsion. Half of the "chimeric" emulsion was individually squirted rapidly through a narrow tip Pasteur pipette into one-dram vials, each containing 2.5 ml of 4% glucose in water and 0.1 ml of lysine free base, 200 mM, and shaken at maximum speed for 3 seconds to form chloroform spherules. The chloroform spherule suspensions were transferred into 250 ml Erlenmeyer flask containing 5 ml of 4% glucose in water and 0.2 ml of lysine free base, 200 mM. A stream of nitrogen gas at 7 L/min was flushed through the flask to evaporate chloroform over 5 minutes at 37 degrees C.

EXAMPLE 3

This example is for the synthesis of heterovesicular liposomes containing ara-C solution as the first aqueous substance and distilled water as the second aqueous substance. For each batch of liposomes prepared, one ml of water containing 100 mg/ml ara-C, pH 1.1 was added into a one-dram vial containing 9.3 umoles of dioleoyl lecithin, 2.1 umoles of dipalmitoyl phosphatidylglycerol, 15 umoles of cholesterol, and 1.8 umoles of triolein and one ml of chloroform, attached to the head of the vortex mixer and shaken at maximum speed for 6 minutes (this is the first water-in-oil emulsion). For the in situ generation of the second water-in-oil emulsion, ½ of the content was removed from the first water-in-oil emulsion, and then 1 ml of distilled water was added into the remaining first water-in-oil emulsion and the one-dram vial was shaken for 10 seconds at maximum speed. This resulted in a "chimeric" water-in-oil emulsion. Half of the "chimeric" emulsion was individually squired rapidly through a narrow tip Pasteur pipette into one-dram vials, each containing 2.0 ml of 4% glucose in water and 0.5 ml of lysine free base, 200 mM, and shaken at maximum speed for 3 seconds to form chloroform spherules. The chloroform spherule suspensions were transferred into 250 ml Erlenmeyer flask containing 4 ml of 4% glucose in water and 0.5 ml of lysine free base, 200 mM. A stream of nitrogen gas at 7 L/min was flushed through the flask to evaporate chloroform over 5 minutes at 37 degrees C.

EXAMPLE 4

Synthesis of Heterovesicular Liposomes Containing Granulocyte-Macrophase Colony Stimulating Factor (GM-CSF)

Exactly the same procedure was used as in Example 2 except IL-2 was replaced with 1 ug of GM-CSF.

EXAMPLE 5

Synthesis of Heterovesicular Liposomes of Various Lipid Composition, and Incorporation of Various Materials into Liposomes In place of using dioleoyl lecithin, dipalmtoyl phosphatidylglyerol, cholesterol, and triolein (TO), and other amphipathic lipids such as phosphatidyl cholines (PC), cardiolipin (CL), dimyristoyl phosphatidylglycerol (DMPG), phosphatidyl ethanolamines (PE), phosphatidyl serines (PS), dimyristoyl phosphatidic acid (DMPA), and other neutral lipids such as tricaprylin (TC) in various combination can be used with similar results. For example, PC/C/CL/TO in 4.5/4.5/1/1 molar ration; DOPC/C/PS/TO in 4.5/4.5/1/1 molar ratio; PC/C/DPPG/TC in 5/4/1/1 molar ratio; PC/C/PG/TC in 5/4/1/1 molar ratio; PE/C/CL/TO in 4.5/4.5/1/1 molar ratio; and PC/C/DMPA/TO in 4.5/4.5/1/1 molar ratio can all be used. To incorporate other water-soluble materials, such as glucose, sucrose, methotrexate, Ponceau S, simply substitute the desired materials for IL-2 in Example 2. Also, other biologically active substances, such as set forth in Table 1, in suitable doses can be similarly substituted for IL-2 as in Example 2.

EXAMPLE 6

In this example, the triolein in lipid components of above examples are substituted either singly or in combination by other triglycerides, vegetable oils, animal fats, tocopherols, tocopherol esters, cholesteryl esthers, or hydrocarbons with good results.

EXAMPLE 7

To make liposomes smaller than that in the foregoing examples, and with reference to Examples 1 or 2, the mechanical strength or duration of shaking or homogenization in Step 4 of Example 1 or 2 was increased. To make liposomes larger, the mechanical strength or duration of shaking or homogenization in Step 4 of Example 1 or 2 was decreased.

The heterovesicular liposomes can be administered to the patients in the normal manner when it is desirable to provide two separate biologically active compounds to the patient for the particular purpose of treatment desired.

The dosage range appropriate for human use includes the range of 1–6000 mg/m to body surface area. The reason that this range is so large is that for some applications, such as subcutaneous administration, the dose required may be quite small, but for other applications, such as intraperitoneal administration, the dose desired to be used may be absolutely enormous. While doses outside the foregoing dose range may be given, this range encompasses the breadth of use for practically all the biologically active substances.

The multivesicular liposomes may be administered by any desired route; for example, intrathecal, intraperitoneal, subcutaneous, intravenous, intralymphatic, oral and submucosal, under many different kinds of epithelia including the bronchialar epithelia, the gastrointestinal epithelia, the urogenital epithelia, and various mucous membranes of the body, and intramuscular.

When encapsulating more than two substances separately in chambers of a liposome, a third (or fourth) aqueous component containing the third or fourth biologically active substance is formed, mixed to form a third or fourth water in oil emulsion, and then combined with the first and second emulsions and mixed to form a "chimeric" emulsion containing the three or more biologically active substances. The remainder of the process is the same as described when encapsulating two biologically active compounds or substances.

The present invention, therefore, obtains the objects and ends and has the advantages mentioned as well as others inherent therein.

While examples of the invention have been given for the purpose of disclosure, changes can be made therein which are within the spirit of the invention as defined by the appended claims.

What is claimed is:

1. A heterovesicular liposome comprising at least two substances of different biological activity each encapsulated in separate chambers of the liposome.

2. The heterovesicular liposome of claim 1 wherein the encapsulated substance comprises a halogenohydroacid.

3. The heterovesicular liposome of claim 2 wherein the halogenohydroacid is selected from the group consisting of hydrochloric acid, hydroiodic acid, hydrobromic acid, hydrofluoric acid, and combinations thereof.

4. The heterovesicular liposome of claim 2 wherein the encapsulated substance comprises a hydrochloride.

5. The heterovesicular liposome of claim 4 wherein the hydrochloride is selected from the group consisting of lysine hydrochloride, histidine hydrochloride, arginine hydrochloride, glucosamine hydrochloride, quanine hydrochloride, and combinations thereof.

6. The heterovesicular liposome of claim 1 wherein the encapsulation is in a buffered medium.

7. A heterovesicular lipid vesicle or liposome produced by: the
  (a) encapsulating a first substance in the presence of an organic solvent by forming a first water-in-oil emulsion from two immiscible components containing a first substance to be encapsulated;
  (b) encapsulating a second substance in the presence of an organic solvent by forming a second water-in-oil emulsion from two immiscible components containing a second substance to be encapsulated;
  (c) encapsulating the product of step (a) and the product of step (b) by dispersing a chimeric emulsion of the product of step (a) and the product of step (b) in a third immiscible aqueous component to form solvent spherules; and
  (d) removing organic solvent from the spherules to form the heterovesicular liposome.

8. The heterovesicular liposome of claims 1 or 7 wherein the biologically active substances are selected from the group consisting of antiasthmatics, cardiac glycosides, antihypertensives, antiparasitics, nucelic acids, antiarrhythmics, antianginas, hormones, antidiabetics, antineoplastics, tranquilizers, steriods, antihistamines, sedatives, analgesics, antibiotics, immunomodulators, antifungals, vasopressors, antivirals, vaccines, monoclonal antibodies, herbicides, neurotransmitters, radionuclides, and radio contrasts.

9. The heterovesicular liposome of claim 1 together with a targeted delivery system.

10. The heterovesicular liposome of claim 9 wherein the liposome is anatomically targeted.

11. The heterovesicular liposome of claim 9 wherein the liposome is mechanistically targeted.

12. The heterovesicular liposome of claim 9 wherein the liposome is passively targeted.

13. The heterovesicular liposome of claim 9 wherein the liposome is actively targeted.

14. The heterovesicular liposome of claim 13 wherein the liposome is actively targeted by coupling with a moiety selected from the group consisting of an antibody, a sugar, a glycolipid, and a protein.

15. A process for producing a heterovesicular lipid vesicle or liposome comprising the steps of:
  (a) encapsulating a first substance in the presence of an organic solvent by forming a first water-in-oil emulsion from two immiscible components containing a first substance to be encapsulated;
  (b) encapsulating a second substance in the presence of an organic solvent by forming a second water-in-oil emulsion from two immiscible components containing a second substance to be encapsulated;
  (c) encapsulating the product of step (a) and the product of step (b) by dispersing a chimeric emulsion of the product of step (a) and the product of step (b) in a third immiscible aqueous component to form solvent spherules; and
  (d) removing organic solvent from the spherules to form the heterovesicular liposome.

16. The process of claim 15, wherein the first substance is encapsulated by providing a first lipid component dissolved in one or more organic solvents and adding into the first lipid component an immiscible first aqueous component containing the first substance and the second substance is encapsulated by providing a second lipid component dissolved in one or more organic solvents and adding into the second lipid component an immiscible second aqueous component containing the second substance.

17. The process according to claim 16 wherein the first and second lipid components are a phospholipid or an admixture of several phospholipids.

18. The process according to claim 17 wherein the phospholipids are selected from the group consisting of phosphatidylcholine, cardiolipin, phosphatidylethanolamine, sphingomyelin, lysophosphatidylcholine, phosphatidylserine, phosphatidylinositol, phosphatidylglycerol, and phosphatidic acid.

19. The process according to claim 17 wherein the one or more of the lipid components contain a lipid with a net negative charge or charges.

20. The process according to claim 17 wherein at least one of the phospholipids are provided in admixture with cholesterol.

21. The process according to claim 17 wherein at least one of the phospholipids are provided in admixture with stearylamine.

22. The process according to claim 15 wherein three or more water-in-oil emulsions containing three or more immiscible aqueous components are combined to form the chimeric emulsion.

23. The process according to claim 16 wherein the first and second lipid components are identical.

24. The process according to claim 16 wherein at least one of the first and second substances is a lipophilic biologically active material.

25. The process according to claim 16 wherein at least one of the first and second lipid components is a neutral lipid.

26. The process according to claim 16 wherein the organic solvent is selected from the group consisting of ethers, hydrocarbons, halogenated hydrocarbons, halogenated ethers, esters, and combinations thereof.

27. The process according to claim 15, wherein at least one substance to be encapsulated is a halogenohydroacid.

28. The process according to claim 27, wherein the halogenohydroacid is selected from the group consisting of hydrochloric acid, hydroiodic acid, hydrobromic acid, hydrofluoric acid and combinations thereof.

29. The process according to claim 15, wherein at least one substance to be encapsulated is a hydrochloride.

30. The process according to claim 29 wherein the hydrochloride is selected from the group consisting of lysine hydrochloride, histidine hydrochloride, arginine hydrochloride, glucosamine hydrochloride, guanine hydrochloride, and combinations thereof.

31. The process according to claim 15 wherein hydrophilic biologically active materials are the substances to be encapsulated.

32. The process according to claim 31 wherein the hydrophilic biologically active materials are selected from the group consisting of interleukin-2, cytosine arabinoside, methotrexate, 5-fluorouracil, cisplatin, floxuridine, melphalan, mercaptopurine, thioguanine, thiotepa, vincristine, vinblastine, streptozocin, leuprolide, interferon, calcitonin, doxorubicin, daunorubicin, mitoxanthrone, amacrine, actinomycin, and bleomycin.

33. The process according to claim 15 wherein the emulsification of the two components is carried out using methods selected from the group consisting of mechanical agitation, ultrasonic energy, and nozzle atomization.

34. The process according to claim 15 wherein the average size and number of the aqueous chambers within the liposome are determined by the type, intensity, and/or duration of the energy used in the formation of the emulsions.

35. The process according to claim 15 wherein the third aqueous component is a buffered medium.

36. The process according to claim 15 wherein the third aqueous component contains a neutralizing agent selected either singly or in combination from the group consisting of free-base lysine and free-base histidine.

37. The process according to claim 35 wherein the third aqueous component is an aqueous solution containing solutes selected from the group consisting of carbohydrates and amino acids.

38. The process according to claim 35 wherein the third aqueous component is an aqueous solution containing solutes selected either singly or in combination from the group consisting of glucose, sucrose, lactose, free-base lysine, and free-base histidine.

39. The process according to claim 15 wherein the dispersion to form solvent spherules is carried out using methods selected from the group consisting of mechanical agitation, ultrasonic energy, and nozzle atomization.

40. The process according to claim 39 wherein the average size of the liposome is determined by the type, intensity, and duration of the energy used.

41. The process according to claim 15 wherein the solvent is removed by evaporation.

42. The process according to claim 41 wherein the evaporation of the organic solvent is provided by passing gas over the second aqueous component.

43. The process of claim 15 wherein the first and second substances to be encapsulated are selected from the group consisting of antiasthmatics, cardiac glycosides, antihypertensives, antiparasitics, nucleic acids and analogs, antiarrhythmics, antianginas, hormones, antidiabetics, antineoplastics, tranquilizers, steroids, antihistamines, sedatives, analgesics, antibiotics, immunomodulators, antifungals, vasopressors, antivirals, vaccines, monoclonal antibodies, herbicides, neurotransmitters, radionuclides, and radio contrasts.

44. A method for the treatment of a patient with at least two biologically active compounds comprising, administering said compounds to the patient each encapsulated in separate chambers in a heterovesicular liposome.

45. A method for the treatment of a patient with at least two biologically active compounds comprising, administering to the patient heterovesicular liposomes encapsulating the biologically active substances according to claims 1 or 14.

46. The process according to claim 25 wherein at least one of the first and second lipid components further comprises a substance selected from the group consisting of vegetable oils, animal fats, tocopherols, tocopherol esters, cholesteryl esters, and hydrocarbons.

* * * * *